United States Patent [19]

Lin et al.

[11] Patent Number: 5,710,141
[45] Date of Patent: *Jan. 20, 1998

[54] METHOD FOR TREATING SKIN WRINKLES

[75] Inventors: Spencer Guang Lin; Kathleen Grieshop Baier, both of Cincinnati, Ohio

[73] Assignee: The Procter & Gamble Company, Cincinnati, Ohio

[*] Notice: The term of this patent shall not extend beyond the expiration date of Pat. No. 5,612,324.

[21] Appl. No.: 724,721

[22] Filed: Sep. 30, 1996

Related U.S. Application Data

[63] Continuation of Ser. No. 422,012, Apr. 12, 1995, Pat. No. 5,612,324, which is a continuation of Ser. No. 287,047, Aug. 8, 1994, abandoned, which is a continuation of Ser. No. 141,434, Oct. 21, 1993, abandoned, which is a continuation of Ser. No. 878,650, May 5, 1992, abandoned.

[51] Int. Cl.$^6$ .................... A61K 31/615; A61K 31/655
[52] U.S. Cl. .................... 514/162; 514/159; 514/859
[58] Field of Search ..................... 514/162, 159, 514/859

[56] References Cited

U.S. PATENT DOCUMENTS

| | | | |
|---|---|---|---|
| 4,318,907 | 3/1982 | Kligman et al. | 424/230 |
| 4,355,028 | 10/1982 | Kligman et al. | 424/230 |
| 4,608,370 | 8/1986 | Aronsohn | 514/159 |
| 4,705,681 | 11/1987 | Maes et al. | 424/70 |
| 4,800,197 | 1/1989 | Kowcz et al. | 514/162 |
| 4,834,076 | 5/1989 | Millet et al. | 128/65 |
| 4,891,227 | 1/1990 | Thaman et al. | 424/443 |
| 4,891,228 | 1/1990 | Thaman et al. | 424/443 |
| 5,015,470 | 5/1991 | Gibson | 424/70 |
| 5,017,367 | 5/1991 | Stojkoski | 424/63 |
| 5,612,324 | 3/1997 | Lin et al. | 514/162 |

FOREIGN PATENT DOCUMENTS

WO 85/04101  9/1985  WIPO.

OTHER PUBLICATIONS

Vitamins & Fine Chemicals for Cosmetics (Handling and Storage of Conditions of Vitamins in Manufacturing of Cosmetics and Toiletries), Hoffmann–La Roche Inc. Technical Bulletin, Sep. 1986.

Ca:110(10): 82270g Apr. 7, 1988.

*Primary Examiner*—Theodore J. Criares
*Attorney, Agent, or Firm*—Darryl C. Little; Loretta J. Henderson; David K. Dabbiere

[57] ABSTRACT

The present invention relates to methods for treating acne and related pilosebaceous disorders with a safe and effective amount of salicylic acid and pantothenic acid or a pantothenic acid derivative. This combination of materials is found to be less irritating and drying to the skin than salicylic acid alone.

2 Claims, No Drawings

METHOD FOR TREATING SKIN WRINKLES

This is a continuation of application Ser. No. 08/422,012, filed on Apr. 12, 1995, now U.S. Pat. No. 5,612,324, which is a continuation of application Ser. No. 08/287,047, filed on Aug. 8, 1994, now abandoned, which is a continuation of application Ser. No. 08/141,434, filed on Oct. 21, 1993, now abandoned which is a continuation of application Ser. No. 07/878,650, filed on May 5, 1992, now abandoned.

TECHNICAL FIELD

The present invention relates to methods for treating acne and related pilosebaceous disorders with a safe and effective amount of salicylic acid and pantothenic acid or a pantothenic acid derivative. This combination is found to be less irritating and drying to the skin than salicylic acid alone. In further embodiments, the present invention also relates to methods for regulating wrinkles and/or atrophy in mammalian skin by treatment with this combination.

BACKGROUND OF THE INVENTION

Acne is a common inflammatory pilosebaceous disease characterized by comedones, papules, pustules, inflamed nodules, superficial pus-filled cysts, and in extreme cases, sinus formation and deep inflammation, sometimes associated with purulent sacs.

The pathogenesis of acne is complex. An interaction between hormones, keratinization, sebum, and bacteria somehow determines the course and severity of the disease. Acne begins at puberty when the increase of androgens causes an increase in the size and activity of the pilosebaceous glands. The earliest microscopic change is intrafollicular hyperkeratosis, which leads to restriction of the pilosebaceous follicle with consequent formation of the comedone composed of sebum, keratin, and microorganisms, particularly *Propionibacterium* (*Corynebacterium*) *acnes*. Lipases from *P. acnes* break down triglycerides in the sebum to form free fatty acids (FFA), which irritate the follicular wall. Retention of sebaceous secretions and dilation of the follicle may lead to cyst formation. Rupture of the follicle with release of the contents into the tissues induces an inflammatory reaction which heals with scarring in severe cases.

Acne tends to appear during puberty and to fade away again, usually spontaneously when growth has stopped. Only rarely does it recede before the age of 20 and occasionally it is still to be found at the age of 30 and beyond. The face, back, and shoulders are the predominant areas affected. Particularly with the face, severe cases can cause alterations resulting in considerable disfigurement with significant psychological burdens for the afflicted person.

Acne can be treated by topical application of various lotions, salves, and the like or by, for example, localized treatment with sulphur, resorcinol, salicylic acid, benzoyl peroxide, vitamin A acids, antibiotics such as erythromycin, and the like.

Salicylic acid is a well recognized anti-acne active ingredient which causes a reduction in intercellular cohesion of the corneocytes (see, C. Huber et al., *Arch. Derm. Res.* 257, pp. 293–297, 1977). It has also been postulated that salicylic works by dissolving the existing keratin plugs as well as preventing the formation of new ones. In order to best exert its skin benefits, the ideal anti-acne composition should deliver and retain optimal concentrations of salicylic acid in the stratum corneum with less penetration through the skin and into the general circulation. Also, compliance by the user to a regimen of treatment involving repeated applications is important. However, salicylic acid tends to be somewhat drying and irritating and can often cause peeling, thereby causing individuals to refrain from using salicylic acid products as frequently and copiously as is necessary to obtain an optimum benefit. Thus, user compliance with current salicylic acid compositions is less than ideal.

Panthenol is the alcohol form of pantothenic acid, a well known nutritional factor. The use of panthenol in skin care products, e.g. shampoos and skin creams is also known. It has been reported that panthenol, for example in combination with zinc oxide, provides an acceleration of superficial wound healing (see, H. Weise et al., "Acceleration of Superficial Wound Healing by Panthenol Zinc Oxide", *Cosmetics and Toiletries*, vol. 103, pp. 79–84, October 1988).

It has been found in the instant invention that the combination of salicylic acid and pantothenic acid or a pantothenic acid derivative, preferably dexpanthenol, provides compositions which are effective for the treatment of acne that are less irritating and drying to the skin than conventional salicylic acid compositions. These compositions have improved user acceptance and thus promote better user compliance with a concomitant overall improved anti-acne benefit. It has also been found that these compositions are useful for effacing and preventing wrinkles and atrophy in mammalian skin.

It is therefore an object of the present invention to provide methods for the treatment of acne in mammalian skin. Another object of the present invention is to provide methods for the treatment of acne which are gentler, and thus less irritating and drying to the skin. A further object of the present invention is to provide methods for the treatment of acne utilizing a combination of the active ingredient salicylic acid with pantothenic acid or a pantothenic acid derivative. An even further object of the present invention is to provide methods for the treatment of acne utilizing a combination of the active ingredient salicylic acid with dexpanthenol. A still further object of the present invention is to provide less irritating compositions for the treatment of acne. A yet further object of the present invention is to provide a method of regulating wrinkles and/or atrophy in mammalian skin.

These and other objects of this invention will become apparent in light of the following disclosure.

SUMMARY OF THE INVENTION

The present invention relates to a method for treating acne in mammalian skin comprising treating the skin with a safe and effective amount of a composition comprising:

(a) from about 0.01% to about 20% salicylic acid, (b) from about 0.1% to about 10% dexpanthenol, and (c) a pharmaceutically-acceptable carrier.

The present invention furthers relates to a method for regulating wrinkles and/or atrophy in mammalian skin.

All percentages and ratios used herein are by weight and all measurements are at 25° C., unless otherwise indicated.

DETAILED DESCRIPTION OF THE INVENTION

Salicylic Acid

An essential component of the compositions useful in the methods of the instant invention is salicylic acid. Salicylic acid, which is also known as 2-hydroxybenzoic acid is a white crystalline powder having a melting point from about 157°–159 ° C. See *The Merck Index*, Tenth Edition, entry 8190, p. 1200 (1983); U.S. Pat. No. 4,514,385, to Damani et al., issued Apr. 30, 1985; and 56 *Federal Register*, pp. 41008–41020, Aug. 16, 1991; these three references are incorporated herein by reference in their entirety.

Without being limited by theory, it is believed salicylic acid provides its anti-acne benefit and its effect on skin wrinkles and/or atrophy via its keratolytic activity.

The salicylic acid of the compositions useful in the instant invention is present from about 0.01% to about 20%, more preferably from about 0.1% to about 7%, and most preferably from about 0.5% to about 2%.

Pantothenic Acid and Pantothenic Acid Derivatives

Another essential component of the compositions useful in the methods of the instant invention is pantothenic acid and/or a pantothenic acid derivative. Pantothenic acid, which is also known as N-(2,4-dihydroxy-3,3-dimethylbutyryl)-B-alanine, is a member of the B complex vitamins and is sometimes known as vitamin $B_3$. Pantothenic acid is a dietary essential for most mammals. The material can exist as the D(+) form, the L(−) form, and the racemate. However, only the natural D(+) form has vitamin activity. See *The Merck Index*, Tenth Edition, entry 6877, p. 1007 (1983); this reference is incorporated herein by reference in its entirety.

A variety of pantothenic acid derivatives are known and or can be synthesized. Nonlimiting examples include the alcohol, aldehyde, alcohol esters, acid esters, and the like. Especially preferred for use in the compositions of the instant invention is the alcohol derivative of pantothenic acid. This alcohol, which is also known as panthenol, pantothenol, and 2,4-dihydroxy-N-(3-hydroxypropyl)-3,3-dimethylbutanamide is a stable source of pantothenic acid activity. Like the parent acid, panthenol can exist as the D(+) form, the L(−) form, and the racemate. However, only the D(+) form has vitamin activity. The D(+) form of panthenol, which is more commonly known as dexpanthenol, is most preferred for use in the instant invention. If however, the racemate is used, it may be necessary to compensate for this factor since the racemate contains only 50% of the D(+) form. See *The Merck Index*, Tenth Edition, entry 2910, p. 426 (1983); this reference is incorporated herein by reference in its entirety.

The pantothenic acid and or pantothenic acid derivative of the compositions useful in the instant invention is present from about 0.1% to about 10%, more preferably from about 0.5% to about 5%, and most preferably from about 1% to about 3.5%.

Preferred for use in these compositions is from about 0.1% to about 10% dexpanthenol, more preferably from about 1% to about 5%, and most preferably from about 1.5% to about 3.5%.

pH Requirements

The pH of a formulation is an important factor in the availability of the salicylic acid and the stability of the formulation. For example, without being limited by theory, at pH values above the $pK_a$ of salicylic acid in a particular matrix, the salicylic acid would exist primarily in its ionized form and would not as readily penetrate into the skin. The following $pK_a$ values have been reported for salicylic acid: 2.98 ($H_2O$) and 7.9 (ethanol). See *CRC Handbook of Chemistry and Physics*, 57th Edition, 1976–1977, p. D-150; and *Lange's Handbook of Chemistry*, 13th Edition, 1985, p. 5–69, respectively. Without being limited by theory, in mixed alcohol water systems, it is believed that the $pK_a$ value for salicylic acid would, in most cases fall between these extremes. An acidic formulation range is preferred for salicylic acid compositions in order to supress ionization and enhance its penetration into the stratum corneum.

A wide variety of acids, bases, and buffers can be utilized to adjust and/or maintain the pH of the compositions useful in the instant invention. Although triethanolamine is preferred, other nonlimiting examples of materials useful for adjusting and/or maintaining the pH include sodium carbonate, sodium hydroxide, hydrochloric acid, phosphoric acid, sodium hydrogen phosphate, sodium dihydrogen phosphate, citric acid, and the like.

The compositions useful in the instant invention preferably have a pH range from about 2 to about 7, more preferably from about 2 to about 6.5, even more preferably from about 2 to about 5.5, and most preferably from about 2.5 to about 4.5.

Pharmaceutically-Acceptable Carriers

The compositions useful in the instant invention comprise a safe and effective amount of a topical pharmaceutically-acceptable carrier or diluent which can be of a variety of different forms. By "safe and effective" is meant an amount sufficient to act as a suitable vehicle for the required components and any other optional components, but not so much as to cause any side effects or skin reactions. "Pharmaceutically-acceptable" means that the carrier is suitable for topical application to the skin without causing any untoward safety or toxicity concerns. In other words, these carriers are suitable for use on mammalian skin. The typical carrier can be in the form of a hydroalcoholic system (e.g. liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems. Nonlimiting examples of the topical carrier systems useful in the present invention are described in the following four references, all of which are incorporated herein by reference in their entirety: "Sun Products Formulary", *Cosmetics & Toiletries*, vol. 105, pp. 122–139 (December 1990); "Sun Products Formulary", *Cosmetics & Toiletries*, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The pharmaceutically-acceptable topical carriers, in total, typically comprise from about 0.1% to about 99.8% by weight of the compositions useful in the present invention, preferably from about 80% to about 99%, and most preferably from about 85% to about 95%.

An especially preferred pharmaceutically-acceptable topical carrier useful in the instant invention is a hydroalcoholic system comprising from about 1% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water.

Optional Components

In addition to the required components of the compositions useful in the present invention, a variety of optional components can also be incorporated.

Other Anti-Acne Agents

The compositions useful in the present invention can also contain other anti-acne agents in addition to the salicylic acid.

These other anti-acne agents preferably comprise from about 0.1% to about 20% by weight of the compositions useful herein, more preferably from about 0.1% to about 10%, and most preferably from about 0.1% to about 5%. Mixtures of these additional anti-acne actives may also be used.

Examples of these other anti-acne agents include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracyclin, triclosan, azelaic acid and its derivatives, phenoxy ethanol and phenoxy proponol, ethylacetate, clindamycin and meclocycline, triclosan, chlorhexidine, tetracycline, neomycin, miconazole hydrochloride, octopirox, parachlorometaxylenol, nystatin, tolnaftate, clotrimazole, and the like); sebostats such as flavinoids; hydroxy acids; antipruritic drugs inlcuding, for example, pharmaceutically-acceptable salts of methdilizine and trimeprazine; and bile salts such as scymnol sulfate and its derivatives, deoxycholate, and cholate.

Also, useful are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Humectants/Moisturizers/Skin Conditioners

A highly preferred optional component of the compositions useful in the instant invention is at least one humectant/moisturizer/skin conditioner. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

Preferred humectants/moisturizers/skin conditioners useful in the compositions of the methods of the present invention are the $C_3$–$C_6$ diols and triols, and also aloe vera gel. Especially preferred is the triol, glycerol, and also aloe vera gel.

Surfactants

The compositions useful in the methods of the present invention can optionally comprise one or more surfactants. The surfactants can be present at a level from about 0.1% to about 10%, more preferably from about 0.2% to about 5%, and most preferably from about 0.2% to about 2.5%. Suitable surfactants include, but are not limited to, nonionic surfactants such as polyalkylene glycol ethers of fatty alcohols, and anionic surfactants such as taurates and alkyl sulfates. Nonlimiting examples of these surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers*, North American Edition (1986), published by Allured Publishing Corporation, which is incorporated herein by reference in its entirety.

Carboxylic Acid Copolymers

Another optional component of the compositions useful in the methods of the instant invention is a carboxylic copolymer (acrylic acid copolymer). Most preferred is Carbomer 1342 (available as Carbopol 1342 from B.F. Goodrich). These polymers are more fully described in U.S. Pat. No. 4,509,949, to Huang et al., issued Apr. 5, 1985, and U.S. Pat. No. 2,798,053, to Brown, issued Jul. 2, 1957, these patents both of which are incorporated herein by reference in their entirety. Also useful are the acrylate/alkyl acrylate crosspolymers such as Acrylates/C10–C30 Alkyl Acrylate Crosspolymer (available as Pemulen TR-1 and Pemulen TR-2 from Goodrich).

These polymers comprise from about 0.025% to about 0.75%, preferably from about 0.05% to about 0.25% and most preferably from about 0.075% to about 0.175% of the compositions useful herein.

Emollients

The compositions useful in the methods of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

Sunscreens

The compositions useful in the methods of the present invention can also optionally comprise at least one sunscreening agent. A wide variety of one or more sunscreening agents are suitable for use in the present invention and are described in U.S. Pat. No. 5,087,445, to Halley et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety.

Preferred among those sunscreens which are useful in the compositions of the instant invention are those selected from the group consisting of ethylhexyl p-methoxycinnamate, octocrylene, octyl salicylate, oxybenzone, and mixtures thereof.

Other useful sunscreens include the solid physical sunblocks such as titanium dioxide (micronized titanium dioxide, 0.03 microns), zinc oxide, silica, iron oxide and the like. Without being limited by theory, it is believed that these inorganic materials provide a sunscreening benefit through reflecting, scattering, and absorbing harmful UV, visible, and infrared radiation.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978, which is incorporated herein by reference in its entirety.

Other Optional Components

A variety of additional ingredients can be incorporated into the compositions useful in the methods of the present invention. Non-limiting examples of these additional ingredients include other vitamins and derivatives thereof (e.g., ascorbic acid, vitamin E, tocopheryl acetate, and the like); thickening agents (e.g. polyacrylamide and $C_{13-14}$ isoparaffin and laureth-7, available as Sepigel from Seppic Corporation); resins; gums; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; copolymers of acrylamide and a cationic acrylate (available as Salcare SC92 from Allied Colloid); emulsifiers; polymers for aiding the film-forming properties and substantivity of the composition (such as a copolymer of eicosene and vinyl pyrrolidone, an example of which is available from GAF Chemical Corporation as Ganex V-220$^R$); preservatives for maintaining the antimicrobial integrity of the compositions; skin penetration aids such as DMSO, 1-dodecylazacycloheptan-2-one (available as Azone from the Upjohn Co.) and the like; artificial tanning agents such as dihydroxyacetone and the like; skin bleaching (or lightening) agents including but not limited to hydroquinone, ascorbic acid, kojic acid and sodium metabisulfite; antioxidants; chelators and sequestrants; and aesthetic components such as fragrances, pigments, colorings, essential oils, skin sensates, astringents, skin soothing agents, skin healing agents and the like, nonlimiting examples of these aesthetic components include clove oil, menthol, camphor, eucalyptus oil, eugenol, menthyl lactate, witch hazel distillate, allantoin, bisabalol, dipotassium glycyrrhizinate and the like.

Delivery Methods for the Compositions

The compositions useful for the methods of the instant invention can be delivered from a variety of delivery devices. The following are two nonlimiting examples.

Medicated Cleansing Pads

The compositions useful herein can be incorporated into a medicated cleansing pad. Preferably these pads comprise from about 50% to about 75% by weight of one or more layers of nonwoven fabric material and from about 20% to about 75% by weight (on dry solids basis) of a water soluble polymeric resin. These pads are described in detail in U.S. Pat. No. 4,891,228, to Thaman et al., issued Jan. 2, 1990 and U.S. Pat. No. 4,891,227, to Thaman et al. issued Jan. 2, 1990; both of which are incorporated by reference herein in their entirety.

Dispensing Devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The valve can include a diaphragm formed from an elastically fluid impermeable material with a plurality of non-intersecting arcuate slits therein, where each slit has a base which is interesected by at least one other slit, and where each slit is out of intersecting relation with its own base, and wherein there is a meanns for disposing the valve in the container inside of the applicator. Examples of these applicator devices are described in U.S. Pat. No. 4,693,623, to Schwartzman, issued Sep. 15, 1987; U.S. Pat. No. 4,620, 648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matic, Mount Vernon, N.Y.

Methods for Treating Acne

The present invention relates to a method for treating acne in mammalian skin. Such a method comprises topically applying to the skin an effective amount of a composition containing salicylic acid and pantothenic acid or a pantothenic acid derivative. The term "effective amount", as used herein, means an amount sufficient to provide an anti-acne benefit. Typically, an effective coating of the skin is from about 0.01 mg salicylic acid or composition of the present invention/$cm^2$ skin to about 5 mg salicylic acid or composition of the present invention/$cm^2$ skin. The composition can be continually applied at appropriate intervals, preferably about once or twice a day until the acne subsides.

Methods for Regulating Wrinkles and/or Skin Atrophy in Mammalian Skin

The present invention also relates to a method for regulating wrinkles and/or atrophy in mammalian skin. Such a method comprises treating the skin with a safe and effective amount of a composition containing salicylic acid and panthothenic acid or a panthothenic acid derivative. The term "effective amount", as used herein, means an amount sufficient to provide a therapeutic effect. Typically, an effective coating of the skin is from about 0.01 mg salicylic acid or composition of the present invention/$cm^2$ skin to about 5 mg salicylic acid or composition of the present invention/$cm^2$ skin.

A preferred method of treating the skin is via chronic topical application. By "chronic" application, it is meant herein that the period of topical application may be over the lifetime of the subject thereby resulting in regulation of wrinkles and/or atrophy in mammalian skin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example I

Composition

A topical composition is prepared by combining the following components utilizing conventional mixing techniques.

| Ingredients | % Weight |
| --- | --- |
| Deionized Water | qs 100 |
| Ethanol (SD 40B Alcohol) | 35.0 |
| Salicylic Acid | 2.0 |
| Dexpanthenol | 3.0 |

In a suitable vessel the salicylic acid is dissolved in the ethanol with stirring. In a separate vessel the dexpanthenol is dissolved in the water with stirring. The resulting alcohol and water solutions are then combined with mixing.

This composition is useful for topical application for the treatment of acne. Alternatively, this composition is useful for topical application to regulate skin wrinkles and/or skin atrophy.

Examples II–V

Composition

The following topical compositions are prepared by combining the following components utilizing conventional mixing techniques.

| | % Weight | | | |
| --- | --- | --- | --- | --- |
| Ingredients | II | III | IV | V |
| Deionized Water | qs 100 | qs 100 | qs 100 | qs 100 |
| Ethanol (SD 40B Alcohol) | 35.0 | 35.0 | 20.0 | 35.0 |
| Salicylic Acid | 2.0 | 2.0 | 0.5 | 2.0 |
| Dexpanthenol | 3.0 | 3.0 | 1.0 | 3.0 |
| Glycerol | 2.0 | 2.0 | — | — |
| Aloe Vera Gel | — | 1.0 | 0.5 | — |
| Menthol | — | — | 0.05 | — |
| Witch Hazel Distillate | — | — | 5.0 | — |
| Na Methyl Cocoyl Taurate or Na Methyl Oleoyl Taurate | — | — | 1.0 | — |
| Isoceteth-20 | — | — | — | 2.0 |
| Quaternium-22 | — | — | 1.0 | — |
| Disodium EDTA | 0.005 | 0.005 | 0.005 | 0.005 |
| Triethanolamine, 99% | 0–1.0 | 0–1.0 | — | 0–1.0 |

In a suitable vessel the salicylic acid is dissolved in the ethanol with stirring. In a separate vessel the remaining ingredients except for the triethanolamine are dissolved in the water with stirring. The resulting alcohol and water solutions are then combined with mixing. Next, sufficient triethanolamine is added as needed to adjust the pH to between about 2.5 to about 4.0.

These compositions are useful for topical application for the treatment of acne. Alternatively, these compositions are useful for topical application to regulate skin wrinkles and/or skin atrophy.

Example VI

Gel Composition

A topical composition is prepared by combining the following components utilizing conventional mixing techniques.

| Ingredients | % Weight |
| --- | --- |
| Deionized Water | qs 100 |
| Ethanol (SD 40B Alcohol) | 40.0 |
| Salicylic Acid | 2.0 |
| Dexpanthenol | 3.0 |
| Polyacrylamide and $C_{13-14}$ Isoparaffin and Laureth-7[1] | 4.0 |

[1] Available as Sepigel from Seppic Corporation.

Water is added to a suitable vessel. While mixing at moderate speed (300 rpm), the polyacrylamide isoparaffin and $C_{13-14}$ isoparaffin and laureth-7 is added to the water. Next the dexpanthenol is added and mixed until dissolved. In a separate vessel, using a Lightnin' or other appropriate mixer with a 3 blade paddle prop, the salicylic acid is added to the ethanol and mixed until dissolved. The alcohol mixture is slowly added with mixing to the water phase to form a gel. The resulting gel is mixed at moderate speed until uniform.

This gel composition is useful for topical application for the treatment of acne. Alternatively, this composition is useful for topical application to regulate skin wrinkles and/or skin atrophy.

Example VII

Gel Composition

A topical composition is prepared by combining the following components utilizing conventional mixing techniques.

| Ingredients | % Weight |
| --- | --- |
| Deionized Water | qs 100 |
| Ethanol (SD 40B Alcohol) | 40.0 |
| Salicylic Acid | 2.0 |
| Dexpanthenol | 3.0 |
| Copolymer of Acrylamide and Cationic Acrylate[1] | 3.0 |
| Menthol | 0.05 |
| Disodium EDTA | 0.05 |
| Glycerol | 2.00 |

[1] Available as Salcare SC92 from Allied Colloids.

Water is added to a suitable vessel. While mixing at moderate speed (300 rpm), the copolymer of acrylamide and cationic acrylate is added to the water. Next the remaining ingredients, except for the salicylic acid, are added and mixed until dissolved. In a separate vessel, using a Lightnin' or other appropriate mixer with a 3 blade paddle prop, the salicylic acid is added to the ethanol and mixed until dissolved. The alcohol mixture is slowly added with mixing to the water phase to form a gel. The resulting gel is mixed at moderate speed until uniform.

This gel composition is useful for topical application for the treatment of acne. Alternatively, this composition is useful for topical application to regulate skin wrinkles and/or skin atrophy.

Example VIII

A Pad of the present invention is made as follows:

| Component | % Weight |
|---|---|
| Substrate A | |
| Cellulose-based nonwoven[1] | 100.0 |
| Substrate B | |
| Polyester (denier = 6)[2] | 45.0 |
| Orlon (denier = 8)[3] | 15.0 |
| Styrene-butadiene resin[4] | 40.0 |
| Laminate | |
| Polyethylene Powder Melt[5] | 100.0 |

[1] Obtained from James River as Airtex Spec 382.
[2] Obtained from Eastern Chemical Company.
[3] Obtained from American Cyanamid.
[4] Obtained from Reichold as tylac 68-500 (ratio of styrene to butadiene 80:20).
[5] Obtained from Quantum Chemical as microthene powder.

Substrate A has a basis weight of about 55 grams per square yard and a loft of about 35 mills. Substrate B has a basis weight of about 65 grams per square yard and a loft of about 70 to 80 mills. The two materials are laminated together by applying a thin coat of polyethylene powder to Substrate A and heating with IR lamps. Substrate A and B are then joined at a nip roll to compress and bond the materials. The resulting nonwoven fabric has a loft of about 90 to 100 mills. The resulting nonwoven fabric is then cut into an oval shape (5 cm×7 cm), or any other desired shape.

The resulting oval pads are suitable for saturation with any of the compositions described in Examples I–VII and are thus suitable for the treatment of acne, or alternatively to regulate skin wrinkles and/or skin atrophy.

Example IX

A soft-tipped applicator product is prepared by placing any of the compositions described in Examples I–VII in a dispensing device having a reservoir. Such devices are described in the patents cited above, and are commercially available from Dab-O-Matic, Mount Vernon, N.Y.

The resulting dispensing products are useful for the treatment of acne, or alternatively to regulate skin wrinkles and/or skin atrophy.

What is claimed is:

1. A method of regulating wrinkles or skin atrophy in mammalian skin comprising treating the skin with a safe and effective amount of a composition comprising:

(a) from about 0.01% to about 20% salicylic acid;

(b) from about 0.1% to about 10% dexpanthenol; and (c) a pharmaceutically acceptable carrier wherein said carrier has a pH of from about 2 to about 6.5.

2. A method of regulating wrinkles or skin atrophy in mammalian skin comprising treating the skin with a safe and effective amount of an irritation reducing composition comprising:

(a) from about 0.01% to about 20% salicylic acid;

(b) from about 0.1% to about 10% dexpanthenol; and (c) a pharmaceutically acceptable carrier wherein said carrier has a pH of from about 2 to about 6.5.

* * * * *

UNITED STATES PATENT AND TRADEMARK OFFICE
CERTIFICATE OF CORRECTION

PATENT NO. : 5,710,141
DATED : January 20, 1998
INVENTOR(S) : Spencer Guang Lin et al.

It is certified that error appears in the above-identified patent and that said Letters Patent is hereby corrected as shown below:

At column 2, line 18 "ache" should read --acne--.
At column 6, line 52 "Halley" should read --Haffey--.

Signed and Sealed this

Thirteenth Day of April, 1999

Attest:

Q. TODD DICKINSON

Attesting Officer

Acting Commissioner of Patents and Trademarks